(12) United States Patent
Shibuya et al.

(10) Patent No.: US 10,296,718 B2
(45) Date of Patent: May 21, 2019

(54) MEDICINE PRODUCTION SUPPORT SYSTEM AND MEDICINE PRODUCTION SUPPORT METHOD

(71) Applicant: HITACHI, LTD., Tokyo (JP)

(72) Inventors: Keisuke Shibuya, Tokyo (JP); Toshiaki Matsuo, Tokyo (JP)

(73) Assignee: HITACHI, LTD., Tokyo (JP)

( * ) Notice: Subject to any disclaimer, the term of this patent is extended or adjusted under 35 U.S.C. 154(b) by 219 days.

(21) Appl. No.: 15/314,633

(22) PCT Filed: May 30, 2014

(86) PCT No.: PCT/JP2014/064461
§ 371 (c)(1),
(2) Date: Nov. 29, 2016

(87) PCT Pub. No.: WO2015/181966
PCT Pub. Date: Dec. 3, 2015

(65) Prior Publication Data
US 2017/0193190 A1    Jul. 6, 2017

(51) Int. Cl.
*G06F 19/00*    (2018.01)
*G06Q 50/22*    (2018.01)
(Continued)

(52) U.S. Cl.
CPC ............ *G06F 19/3462* (2013.01); *A61J 3/00* (2013.01); *A61K 9/00* (2013.01); *C12N 5/06* (2013.01);
(Continued)

(58) Field of Classification Search
CPC ............ G06F 19/3462; G06F 19/3456; A61M 2205/52; A61M 2205/6009; A61J 3/00; A61K 9/00; C12N 5/06
(Continued)

(56) References Cited

U.S. PATENT DOCUMENTS 7,379,784 B2    5/2008    Popp
7,392,107 B2    6/2008    Popp
(Continued)

FOREIGN PATENT DOCUMENTS

EP    2051223 A1    4/2009
JP    2002-157473 A    5/2002
(Continued)

OTHER PUBLICATIONS

The European Search Report dated Dec. 11, 2017 for the European Application No. EP20140893264.
(Continued)

*Primary Examiner* — Michael Collins
(74) *Attorney, Agent, or Firm* — Volpe and Koenig, P.C.

(57) ABSTRACT

In order to improve variety of medicines producible, a central control device that controls a plant control device for controlling a cell culture environment of a cell strain for producing a medicine is installed in a pharmaceutical manufacturing plant for manufacturing a medicine. The central control device controls the plant control device on the basis of analysis data relevant to an inspection result of a patient. The central control device transmits traffic information to a navigation device, and the navigation device searches for a delivery route of a delivery vehicle for delivering a medicine on the basis of the transmitted traffic information.

19 Claims, 11 Drawing Sheets

(51) Int. Cl.
*C12N 5/07* (2010.01)
*A61J 3/00* (2006.01)
*A61K 9/00* (2006.01)
*G06Q 50/24* (2012.01)

(52) U.S. Cl.
CPC ............ *G06Q 50/22* (2013.01); *G06Q 50/24* (2013.01); *A61M 2205/52* (2013.01); *A61M 2205/6009* (2013.01); *G06F 19/3456* (2013.01)

(58) Field of Classification Search
USPC ................................................ 700/231–244
See application file for complete search history.

(56) References Cited

U.S. PATENT DOCUMENTS

| | | | |
|---|---|---|---|
| 7,617,057 B2* | 11/2009 | May ................. | A01G 7/00 702/62 |
| 7,799,273 B2 | 9/2010 | Popp | |
| 7,987,632 B2* | 8/2011 | May ................. | A01G 7/00 47/17 |
| 9,606,553 B2* | 3/2017 | Faris ................ | G05D 27/02 |
| 2002/0046290 A1 | 4/2002 | Andersson et al. | |
| 2004/0132199 A1* | 7/2004 | Manabe ............ | G01N 31/22 436/94 |
| 2004/0172169 A1* | 9/2004 | Wright, IV ...... | A61J 3/074 700/265 |
| 2005/0216142 A1 | 9/2005 | Herzog et al. | |
| 2007/0021856 A1 | 1/2007 | Popp | |
| 2007/0289207 A1* | 12/2007 | May ................. | A01G 7/00 47/17 |
| 2008/0210610 A1* | 9/2008 | Whiteman ........ | C02F 3/12 210/143 |
| 2009/0143964 A1 | 6/2009 | Navone et al. | |
| 2010/0122739 A1* | 5/2010 | Williamson ...... | C02F 1/008 137/395 |
| 2010/0217425 A1 | 8/2010 | Popp | |
| 2012/0158610 A1 | 6/2012 | Botvinick et al. | |
| 2013/0073387 A1* | 3/2013 | Heath .............. | G06Q 30/02 705/14.53 |
| 2014/0127802 A1 | 5/2014 | Goh et al. | |
| 2015/0351326 A1* | 12/2015 | D'Aoust ........... | A01G 22/00 47/1.5 |
| 2016/0245759 A1 | 8/2016 | Popp | |

FOREIGN PATENT DOCUMENTS

| | | |
|---|---|---|
| JP | 2002-197189 A | 7/2002 |
| JP | 2006-185161 A | 7/2006 |
| JP | 2009-009294 A | 1/2009 |
| JP | 2013-535756 A | 9/2013 |
| WO | 2012/021899 A2 | 2/2012 |

OTHER PUBLICATIONS

Summons to attend oral proceedings pursuant to Rule 115(1) EPC dated Jan. 3, 2019 for the European Patent Application No. 14893264.3.

* cited by examiner

MEDICINE PRODUCTION SUPPORT SYSTEM AND MEDICINE PRODUCTION SUPPORT METHOD

TECHNICAL FIELD

The present invention relates to techniques of a medicine production support system and a medicine production support method which support production of a medicine.

BACKGROUND ART

Like an advancement of aging societies, an increase in lifestyle-related diseases, an increase in national medical care costs, and the like, environments in medical fields have greatly varied. On the other hand, there is movement for personalized medical care in which an optimal treatment for each individual patient is set in consideration of genetic backgrounds, physical states, disease states, and the like of patients.

In general, a patient feeling abnormality of a body goes to a hospital, is inspected in the hospital, and takes medical advice of a doctor on the basis of the inspection result. The patient takes a prescription of surgery or medicine if necessary. On the other hand, in personalized medical care, in order to take medical care suitable for each individual person, gene information or metabolites in the body of the person are measured through the inspection, information which has been scientifically verified is compared, and a doctor determines a treatment or medicines to be administered.

More specifically, a doctor determines a medicine suitable for the patient using a companion diagnostic agent and administers a medicine with a great medicinal effect and a small side effect to the patient. In the personalized medical care, since properties of medicines are changed from medicines effective in all people to medicines suitable for individual persons, production of producing one kind of medicine in quantity is expected to be changed to production of producing large-variety medicines in small quantity. At this time, pharmacies have difficulty in managing stocks of small-quantity and large-variety medicines and thus there is a need for new production and distribution systems for the personalized medical care.

Regarding quality of medicines, conventional medicines have only to be effective for all people and have small side effects and thus may be allowed even when the medicines are not completely homogenous. For example, in an antibody medicine, the antibody medicine is produced using animal cells, but sugar chains to be modified to the medicine in the animal cells have a distribution and thus a homogenous medicine is not necessarily produced. Accordingly, conventional medicines are allowed as long as the glycosylation is maintained in a constant distribution. However, the glycosylation contributes to a medicinal effect and there is also a danger of a side effect for each person. Therefore, in the personalized medical care, it is necessary to further perform quality control of the glycosylation.

Such a personalized medical care technique is disclosed in PTL 1.

PTL 1 discloses a system and a method for producing personalized medicines in which information on a patient is received and medicine compounding, that is, mixture of produced medicines, is controlled on the basis of the received information.

CITATION LIST

Patent Literature

PTL 1: JP 2013-535756 A

SUMMARY OF INVENTION

Technical Problem

In the technique described in PTL 1, since mixture of produced medicines is controlled, there is a limit in the variety of medicines producible.

The present invention is made in consideration of the above-mentioned circumstances and an object of the present invention is to improve variety of medicines producible.

Solution to Problem

In order to achieve the above-mentioned object, according to the present invention, there is provided a medicine production support system including: a plant control device that controls a cell culture environment of a cell strain for producing a medicine in a pharmaceutical manufacturing plant for producing the medicine; and a central control device that controls the plant control device on the basis of information input from outside.

Advantageous Effects of Invention

According to the present invention, it is possible to improve variety of medicines producible.

DESCRIPTION OF EMBODIMENTS

Hereinafter, modes for carrying out the present invention (referred to as "embodiments") will be described in detail with appropriate reference to the accompanying drawings.

First Embodiment

Figure 1:
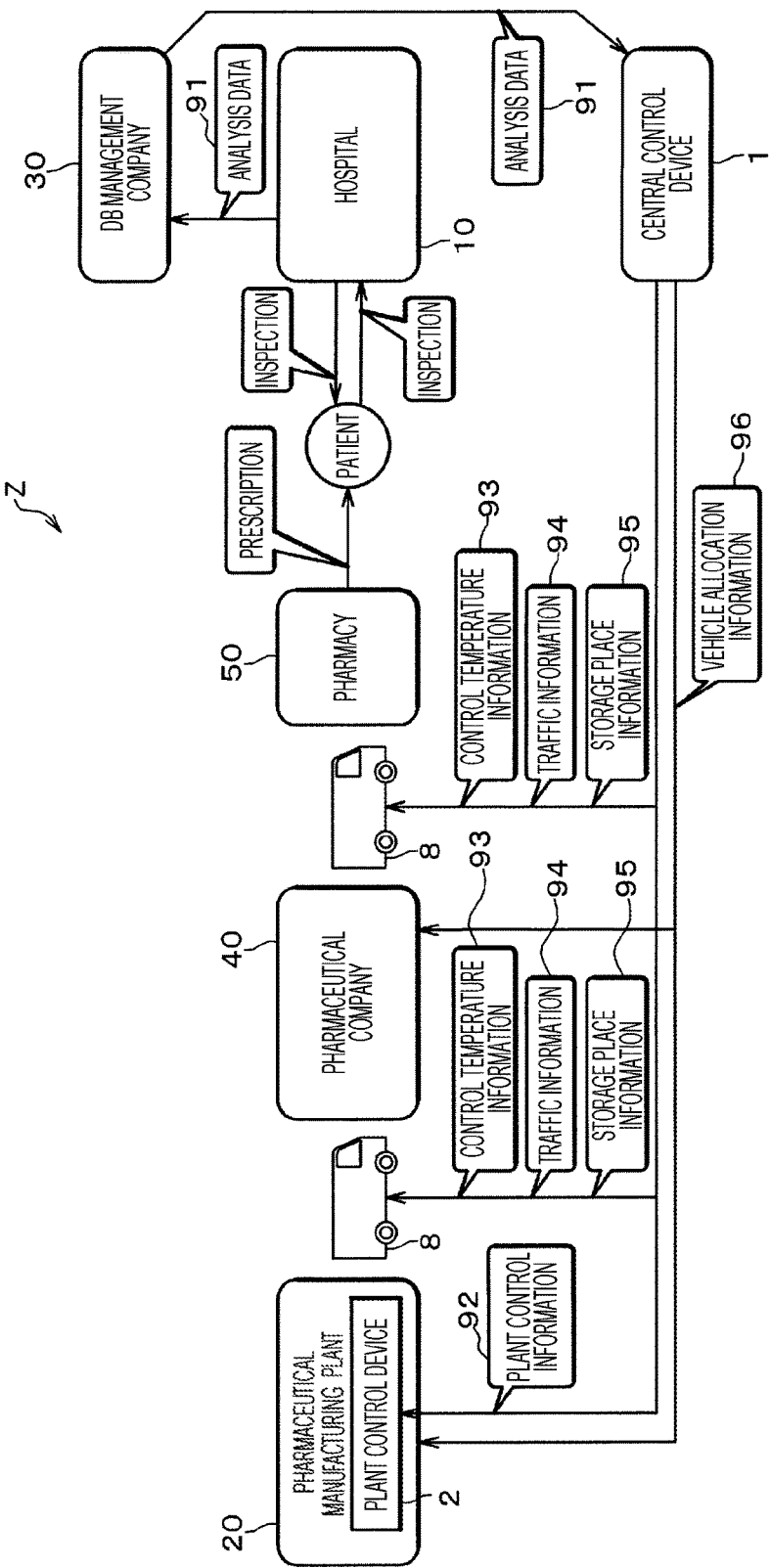
FIG. 1 is a diagram illustrating an example of a configuration of a medicine production support system according to a first embodiment.
Figure 2:
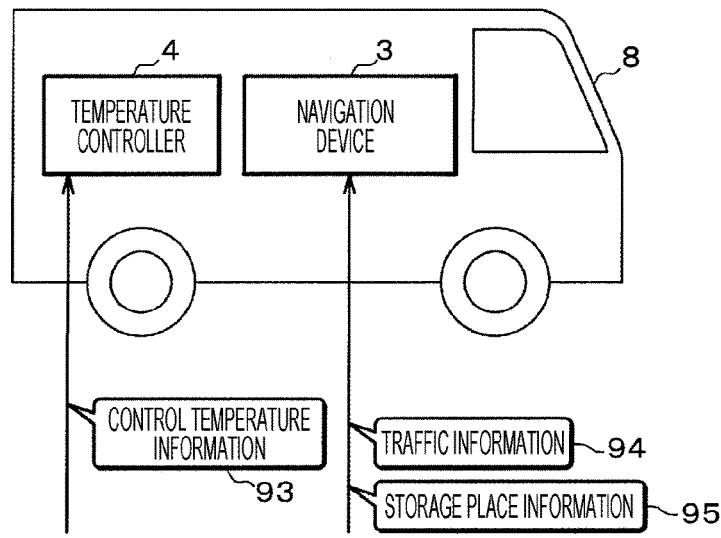
FIG. 2 is a diagram illustrating an example of a configuration of a delivery vehicle according to the embodiment.

First, a first embodiment of the present invention will be described with reference to FIGS. 1 to 12.
<System Configuration>
FIG. 1 is a diagram illustrating an example of a configuration of a medicine production support system according to the first embodiment, and FIG. 2 is a diagram illustrating an example of a configuration of a delivery vehicle according to this embodiment.

A medicine production support system Z includes a central control device (a control device) 1, a plant control device 2 that is installed in a pharmaceutical manufacturing plant 20, a navigation device (a route search device) 3 that is installed in a delivery vehicle 8, and a temperature controller 4.

The central control device 1 acquires analysis data 91 which is generated on the basis of an inspection result of a patient. The central control device 1 generates plant control information 92 for controlling a medicine producing plant in the pharmaceutical manufacturing plant 20 on the basis of the acquired analysis data 91. The central control device 1 generates control temperature information 93 which is information on a storage temperature of a medicine in the delivery vehicle 8, traffic information 94 which is information on a traffic situation, or storage place information 95 which is information on a storage place of the produced medicine. The central control device 1 transmits the generated plant control information 92 to the plant control device 2 of the pharmaceutical manufacturing plant 20, transmits the generated traffic information 94 to the navigation device 3 of the delivery vehicle 8, or transmits the generated control temperature information 93 to the temperature controller 4.

The plant control device 2 is installed in the pharmaceutical manufacturing plant 20, and controls the medicine producing plant of the pharmaceutical manufacturing plant 20 when the plant control information 92 is acquired from the central control device 1. In this way, the central control device 1 remotely controls the plant control device 2.

The navigation device 3 is installed in the delivery vehicle 8 for delivering a medicine, and searches for an optimal delivery route on the basis of the traffic information 94 or the storage place information 95 acquired from the central control device 1.

The temperature controller 4 is installed in the delivery vehicle 8 for delivering a medicine, and controls the temperature of a medicine storage cabinet in the delivery vehicle 8 on the basis of the control temperature information 93 acquired from the central control device 1.
(Flow)
First, when a patient is inspected in an inspection agency such as a hospital 10, the hospital 10 transmits the inspection result as the analysis data 91 to a database (DB) management company 30. The DB management company 30 stores the analysis data 91 in a DB which is not illustrated and transmits the analysis data 91 to the central control device 1.

As described above, the central control device 1 generates the plant control information 92, the control temperature information 93, or the storage place information 95 on the basis of the acquired analysis data 91. As described above, the central control device 1 also generates the traffic information 94.

Specifically, the central control device 1 can refer to data (medicine data) in which the analysis data 91 and proper medicines (with a high medicinal effect and a low side effect) are correlated with each other.

The central control device 1 selects a proper medicine on the basis of the reference result and generates the plant control information 92 which is control information of the medicine producing plant required for producing the medicine.

The plant control information 92 includes information such as a temperature, pH, dissolved oxygen, and nutrient concentration in the medicine producing plant. The central control device 1 calculates a priority order on the basis of the date and the quantity in which the medicine has to be administered to a patient and which is included in the analysis data 91, and generates a medicine production time schedule to produce the medicine on the basis of the calculated priority order. The central control device 1 adds information on the generated time schedule to the plant control information 92.

When plural medicine producing facilities 20 are present, the central control device 1 optimizes the plant control information 92 for producing a medicine on the basis of data such as production scales in the medicine producing facilities, producible medicines, and distribution routes.

Then, the central control device 1 transmits the generated plant control information 92 to the plant control device 2 of pharmaceutical manufacturing plant 20 and transmits the control temperature information 93 to the temperature controller 4 installed in the delivery vehicle 8.

The plant control device 2 of the pharmaceutical manufacturing plant 20 controls the medicine producing plant on the basis of the plant control information 92 transmitted from the central control device 1 so as to produce a medicine.

When the plant control information 92 is received from the central control device 1 via a communication network, the plant control device 2 installed in the pharmaceutical manufacturing plant 20 controls a medicine producing process on the basis of the received plant control information 92. Here, since the analysis data 91 includes private data, the data is converted into a format not including the private information by the information converting unit 117 of the central control device 1 at the time of transmitting the data from the central control device 1 to the outside. In the pharmaceutical manufacturing plant, a proper producing process may vary depending on medicines and details thereof will be described later.

Thereafter, the produced medicine is sent to a pharmaceutical company 40 and a pharmacy 50 and is prescribed to a patient.

The central control device 1 determines allocation of a delivery vehicle 8 on the basis of transportation conditions such as control temperatures of medicines, fragileness, and expiry dates of medicines or a type of a medicine storage cabinet mounted on the delivery vehicle 8. Then, the central control device 1 transmits vehicle allocation information 96 to a vehicle allocation information display device 5 (FIG. 7) installed in the pharmaceutical manufacturing plant 20 or the pharmaceutical company 40.

(Distribution)

When medicine transports, it is necessary to control the temperature optimally.

Appropriate temperature control is required to transport a medicine.

In the medicine production support system Z according to this embodiment, since a scheduled shipping date, a shipping quantity, and the like of a medicine to be produced can be seen, it is possible to understand a transportation environment of the medicine scheduled to be shipped. Since the delivery vehicle 8 to be prepared varies depending on the transportation environment, the delivery vehicle is prepared by the central control device 1. Therefore, the allocation of delivery is performed by the delivery vehicle 8 using delivery information. Transportation temperature control of a medicine is performed in four steps of room temperature, cold place, cold storage, and freezer storage. Since the room temperature is equal to or lower than 30° C., cooling in the summer is essential in many areas of Japan. Since there is a possibility of freezing in the winter, the medicine needs to be managed warm using heating. The temperature control of a medicine affects labor environments of distribution spots.

In actual temperature control, it is preferable that an air-conditioner be set to a constant temperature and the temperature be measured using a thermometer installed in the delivery vehicle 8. At this time, a temperature recorder may be of an analog type in which the temperature is recorded on a sheet of paper or the temperature may be normally monitored using a digital thermometer.

In transportation of a medicine from the pharmaceutical manufacturing plant 20 to a medicine storehouse of the pharmaceutical company 40 and delivery of a medicine from the medicine storehouse of the pharmaceutical company 40 to a pharmacy 50, the navigation device 3 installed in the delivery vehicle 8 searches various transportation routes for an optimal delivery route and specifies the delivery route. Such search and specification are performed by carrying out information technology such as simulation software or a digital map in the navigation device 3 using information such as the time schedule or the like.

Particularly, in personalized medical care, since a medicine to be produced needs to be delivered to each patient, it is important to optimize the delivery route for each patient.

In a medicine distribution service, maintenance of a stable supply network is indispensable in view of characteristics of a product as a medicine. That is, even when earthquake disaster or the like occurs, it is necessary to construct a rapid and stable supply system. In the medicine production support system Z according to this embodiment, the navigation device 3 searches for and specifies an optimal delivery route on the basis of information of a road situation acquired from a traffic information 94 center or the like. Accordingly, the medicine production support system Z according to this embodiment can understand a disaster situation and derive a transportable distribution route at the time of disaster such as earthquake disaster.

Hereinafter, the devices 1 to 5 will be appropriately described with reference to FIGS. 1 and 2.

<Central Control Device>

Figure 3:
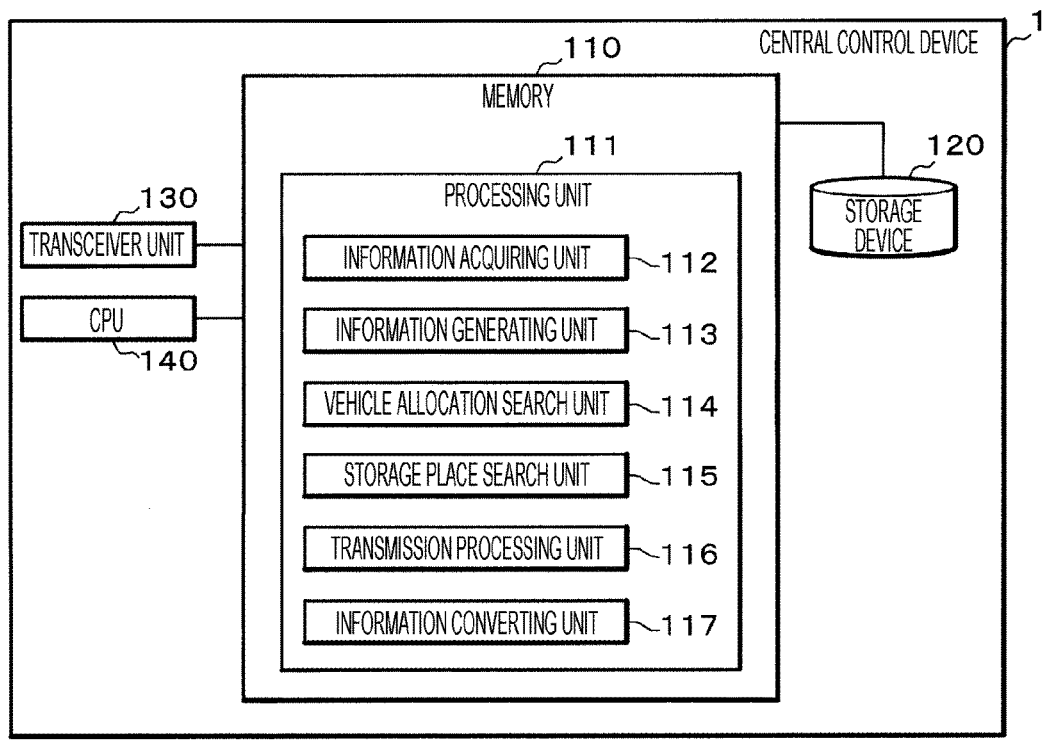
FIG. 3 is a functional block diagram illustrating an example of a configuration of a central control device according to the embodiment.

FIG. 3 is a functional bloc diagram illustrating an example of a configuration of the central control device according to this embodiment.

The central control device 1 includes a memory 110, a storage device 120, a transceiver unit 130 such as a network interface card (NIC), and a central processing unit (CPU) 140.

A program stored in the storage device 120 is loaded into the memory 110 and is executed by the CPU 140, whereby a processing unit 111 and an information acquiring unit 112, an information generating unit 113, a vehicle allocation search unit 114, a storage place search unit 115, a transmission processing unit 116, and an information converting unit 117 constituting the processing unit 111 are embodied.

The processing unit 111 controls the units 112 to 117.

The information acquiring unit 112 acquires the analysis data 91 and the like from the outside.

The information generating unit 113 generates the plant control information 92 or generates the control temperature information 93, the traffic information 94, or the like on the basis of the acquired analysis data 91 and the like.

The vehicle allocation search unit 114 searches for and determines allocation of a delivery vehicle on the basis of the analysis data 91.

The storage place search unit 115 searches for a storage place such as an empty storehouse on the basis of the analysis data 91.

The transmission processing unit 116 transmits the plant control information 92, the control temperature information 93, the traffic information 94, or the storage place information 95 to the plant control device 2, the navigation device 3, or the temperature controller 4.

The information converting unit 117 converts information transmitted to the outside into information which cannot be referred to for private information of a patient. Specifically, private information of a patient is deleted from the information transmitted to the outside.

<Plant Control Device>

Figure 4:
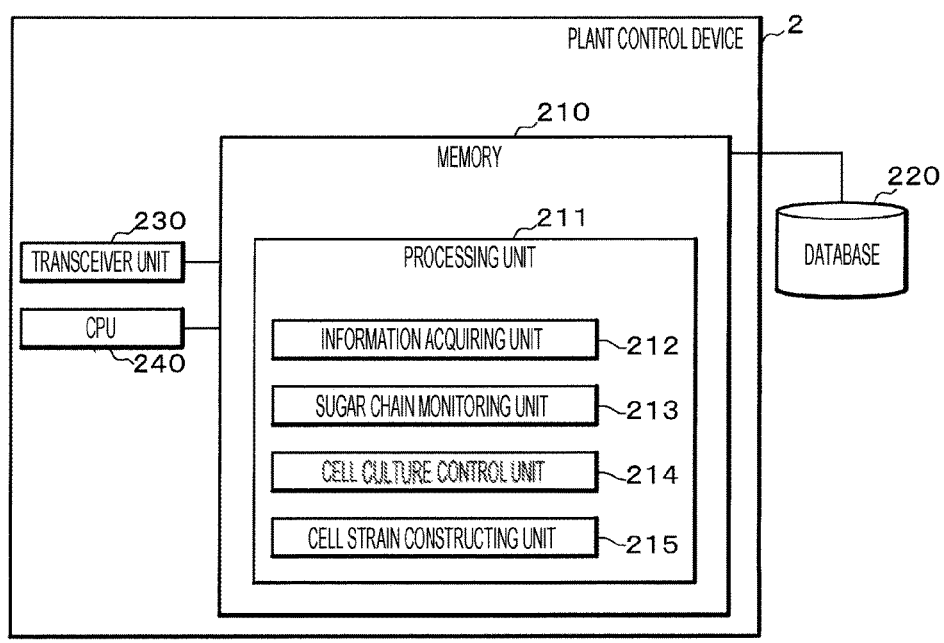
FIG. 4 is a functional block diagram illustrating an example of a configuration of a plant control device according to the embodiment.

FIG. 4 is a functional block diagram illustrating an example of a configuration of the plant control device according to this embodiment.

The plant control device 2 includes a memory 210, a transceiver unit 230 such as NIC, and a CPU 240. The plant control device 2 is connected to a database 220 in which cell culture environment information in which a sugar chain concentration in a bioreactor and environment information in the bioreactor are correlated with each other or the like is stored.

A program stored in the database 220 is loaded into the memory 210 and is executed by the CPU 240, whereby a processing unit 211 and an information acquiring unit 212, a sugar chain monitoring unit 213, a cell culture environment control unit 214, and a cell strain constructing unit 215 constituting the processing unit 211 are embodied.

The processing unit 211 controls the units 212 to 214.

The information acquiring unit 212 acquires the plant control information 92 and the like from the central control device 1.

The sugar chain monitoring unit 213 monitors a concentration of a sugar chain (a sugar chain concentration) included in antibody protein produced in the bioreactor. The sugar chain monitoring unit 213 refers to the cell culture environment information stored in the database 220 using the monitoring result of the sugar chain concentration as a key and transmits the cell culture environment to the cell culture environment control unit 214.

The cell culture environment control unit 214 controls the environment of the bioreactor on the basis of the cell culture environment information or the like transmitted from the sugar chain monitoring unit 213.

The cell strain constructing unit 215 controls generation of a cell strain causing a high medicinal effect to be described later.

<Navigation Device>

Figure 5:
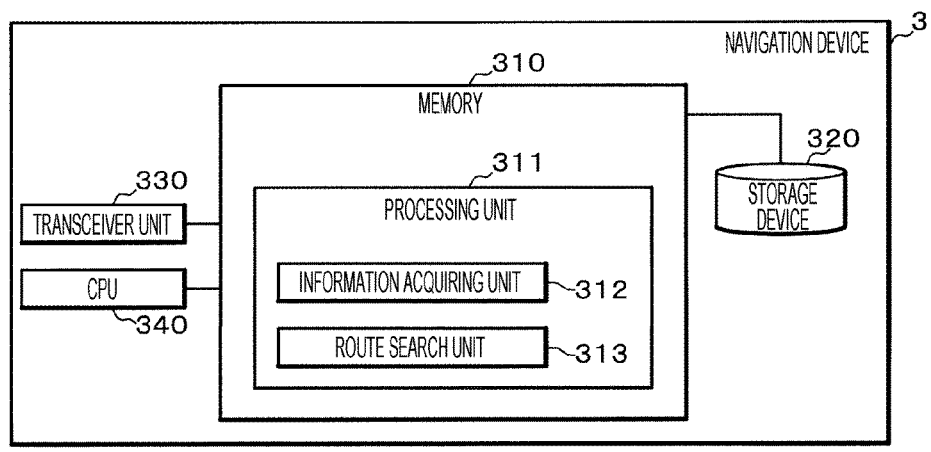
FIG. 5 is a functional block diagram illustrating an example of a configuration of a navigation device according to the embodiment.

FIG. 5 is a functional block diagram illustrating an example of a configuration of the navigation device according to this embodiment.

The navigation device 3 includes a memory 310, a storage device 320, a transceiver unit 330 such as NIC, and a CPU 340.

A program stored in the storage device 320 is loaded into the memory 310 and is executed by the CPU 340, whereby a processing unit 311 and an information acquiring unit 312 and a route search unit 313 constituting the processing unit 311 are embodied.

The processing unit 311 controls the units 312 and 313.

The information acquiring unit 312 acquires the traffic information 94, the storage place information 95, and the like from the central control device 1.

The route search unit 313 searches for a route to a destination on the basis of the storage place information 95, the traffic information 94, and the like acquired from the central control device 1.

<Temperature Controller>

Figure 6:
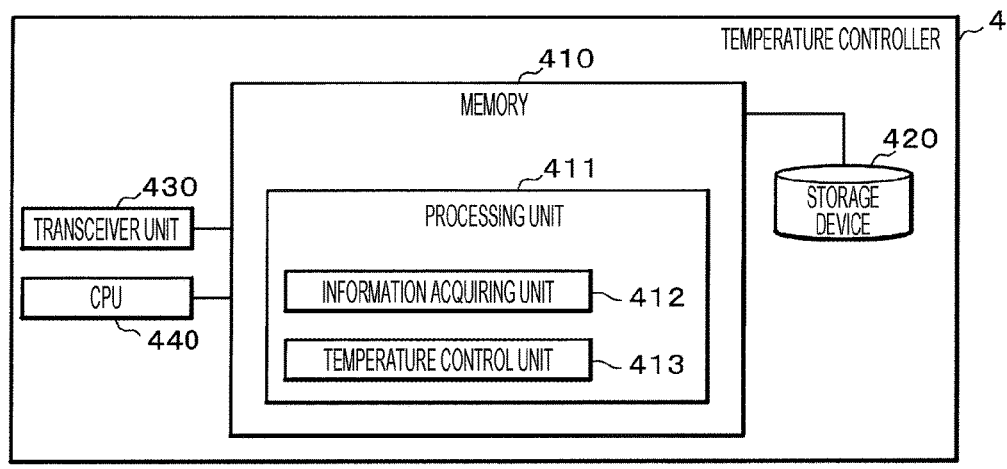
FIG. 6 is a functional block diagram illustrating an example of a configuration of a temperature controller according to the embodiment.

FIG. 6 is a functional block diagram illustrating an example of a configuration of the temperature controller according to this embodiment.

The temperature controller 4 includes a memory 410, a storage device 420, a transceiver unit 430 such as NIC, and a CPU 440.

A program stored in the storage device 420 is loaded into the memory 410 and is executed by the CPU 440, whereby a processing unit 411 and an information acquiring unit 412 and a temperature control unit 413 constituting the processing unit 411 are embodied.

The processing unit 411 controls the units 412 and 413.

The information acquiring unit 412 acquires the control temperature information 93 and the like from the central control device 1.

The temperature control unit 413 controls the temperature of a medicine storage cabinet (not illustrated) installed in the delivery vehicle 8 on the basis of the control temperature information 93 and the like acquired from the central control device 1.

<Vehicle Allocation Information Display Device>

Figure 7:
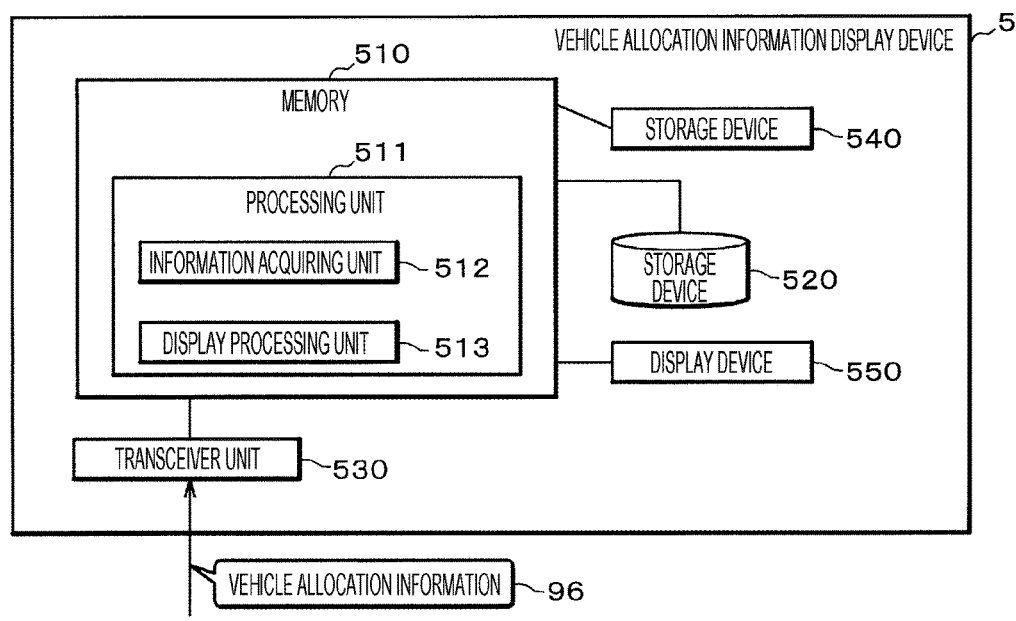
FIG. 7 is a functional block diagram illustrating an example of a configuration of a vehicle allocation information display device according to the embodiment.

FIG. 7 is a functional block diagram illustrating an example of a configuration of the vehicle allocation information display device according to this embodiment.

The vehicle allocation information display device 5 includes a memory 510, a storage device 520, a transceiver unit 530 such as NIC, a CPU 540, and a display device 550 such as a display.

A program stored in the storage device 520 is loaded into the memory 510 and is executed by the CPU 540, whereby a processing unit 511 and an information acquiring unit 512 and a display processing unit 513 constituting the processing unit 511 are embodied.

The processing unit 511 controls the units 512 and 513.

The information acquiring unit 512 acquires the vehicle allocation information 96 and the like from the central control device 1 via the transceiver unit 530.

The display processing unit 513 presents a user details of the vehicle allocation information 96 by displaying details of the vehicle allocation information 96 and the like acquired from the central control device 1 on the display device 550.

The user allocates the delivery vehicle 8 depending on details of the vehicle allocation information 96 displayed on the display device 550.

<Process Flow>

Figure 8:
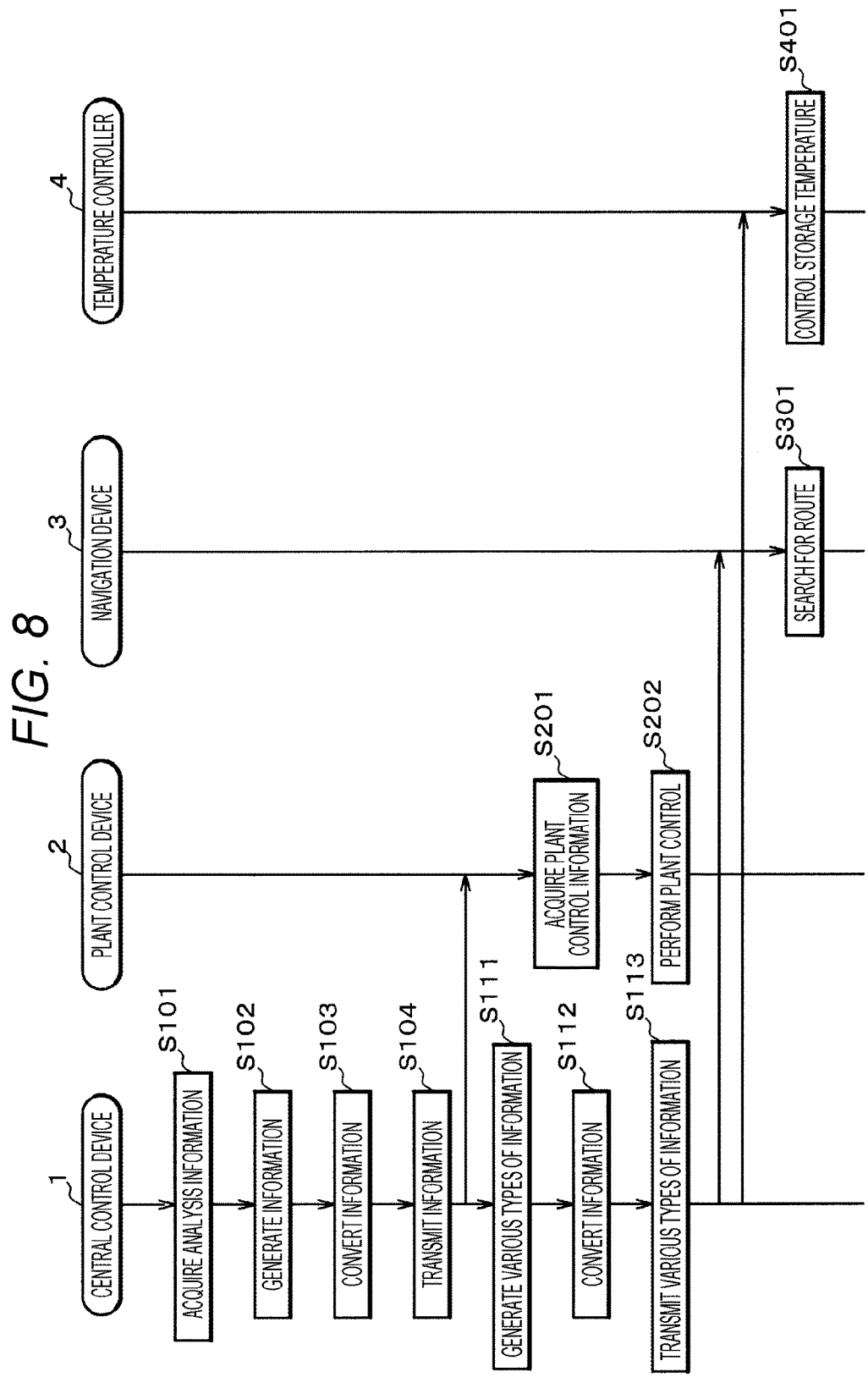
FIG. 8 is a diagram illustrating an operation sequence of a medicine production control system according to the embodiment.

FIG. 8 is a diagram illustrating an operation flow of the medicine production support system according to this embodiment. Hereinafter, FIGS. 1 to 6 will be appropriately referred to.

First, the information acquiring unit 112 of the central control device 1 acquires analysis data 91 of inspection from the DB management company 30 (S101).

Then, the information generating unit 113 of the central control device 1 generates plant control information 92 on the basis of the acquired analysis data 91 (S102).

Then, the information converting unit 117 of the central control device 1 performs information conversion of deleting private information of a patient from the generated plant control information 92 (S103).

The transmission processing unit 116 of the central control device 1 transmits the converted plant control information 92 (information) to the plant control device 2 (S104).

The information acquiring unit 212 of the plant control device 2 acquires the plant control information 92 from the central control device 1 (S201).

The cell culture environment control unit 214 or the sugar chain monitoring unit 213 of the plant control device 2 performs plant control of controlling the units (the bioreactor and the like) of the medicine producing plant on the basis of the plant control information 92 (S202). The plant control will be described later.

The storage place search unit 115 of the central control device 1 searches for and determines allocation of a delivery vehicle 8 or a storage place of a medicine on the basis of the analysis data 91, storage place list data (not illustrated) stored in the storage device 120, or the like. The information generating unit 113 of the central control device 1 generates storage place information 95 on the basis of the storage place search result of the medicine.

The information acquiring unit 112 of the central control device 1 acquires traffic information 94 from a traffic center (not illustrated) and the information generating unit 113 sets the acquired traffic information 94 as the traffic information 94 to be transmitted to the navigation device 3.

In addition, the information generating unit 113 of the central control device 1 generates control temperature information 93 which is information on a storage temperature at the time of delivery of a medicine on the basis of the analysis data 91.

The vehicle allocation search unit 114 searches for and determines allocation of a delivery vehicle 8 on the basis of the acquired analysis data 91 and a transportation condition stored in advance in the storage device 120. Here, the transportation condition includes control temperatures of medicines, fragileness, and expiry dates of medicines. The information generating unit 113 sets information on the determined allocation of the delivery vehicle 8 as the vehicle allocation information 96. The vehicle allocation information 96 includes an identification number of the delivery vehicle 8 to be used or the like.

In this way, the information generating unit 113 of the central control device 1 generates various types of information such as the storage place information 95, the traffic information 94, the control temperature information 93, and the vehicle allocation information 96 (S111).

Thereafter, the information converting unit 117 of the central control device 1 performs information conversion of deleting private information of a patient from the generated storage place information 95, the generated traffic information 94, the generated control temperature information 93, and the generated vehicle allocation information 96 (S112).

Then, the transmission processing unit 116 of the central control device 1 transmits information such as the traffic information 94 and the storage place information 95 to the navigation device 3 of the delivery vehicle B. In addition, the transmission processing unit 116 of the central control device 1 transmits information such as the control temperature information 93 to the temperature controller 4. In addition, the transmission processing unit 116 of the central control device 1 transmits information such as the vehicle allocation information 96 to the pharmaceutical manufacturing plant 20 or the pharmaceutical company 40. In this way, the transmission processing unit 116 transmits various types of information (S113).

The route search unit 313 of the navigation device 3 searches for a route on the basis of the received traffic information 94 or the received storage place information 95 (S301).

The temperature control unit 413 of the temperature controller 4 controls the temperature of a medicine storage cabinet installed in the delivery vehicle 8 on the basis of the control temperature information 93 (S401).

The vehicle allocation information 96 transmitted from the central control device 1 is input to the vehicle allocation information display device 5 and details of the vehicle allocation information 96 is displayed on the display device 550 by the display processing unit 513 of the vehicle allocation information display device 5, but this process is not illustrated in FIG. 8.

<Control of Medicine Producing Process>

In the medicine production in personalized medical care, production of higher quality pharmaceuticals is required. Antibody protein that is most anticipated as a molecular target drug for personalized medicine is often generally produced by culturing an animal cell. The efficacy and quality of such an antibody protein as a change as the modification of a molecule called carbohydrate chain is conducted in the animal cell to be cultured.

The control of such glycosylation is generally significantly difficult, and it is greatly affected by the cell strain to be used in the medicine production or the operation process to culture the cell. General antibody drugs that are currently used are intended to be a drug effective for all people, and thus the variation in glycosylation to a certain extent is acceptable. On the other hand, in the personalized medicine, the effect or side effect of the drug to each individual is greatly different depending on the glycosylation state, and thus the cell strain and culture operation process which are able to realize the intended glycosylation are significantly important.

Figure 9:
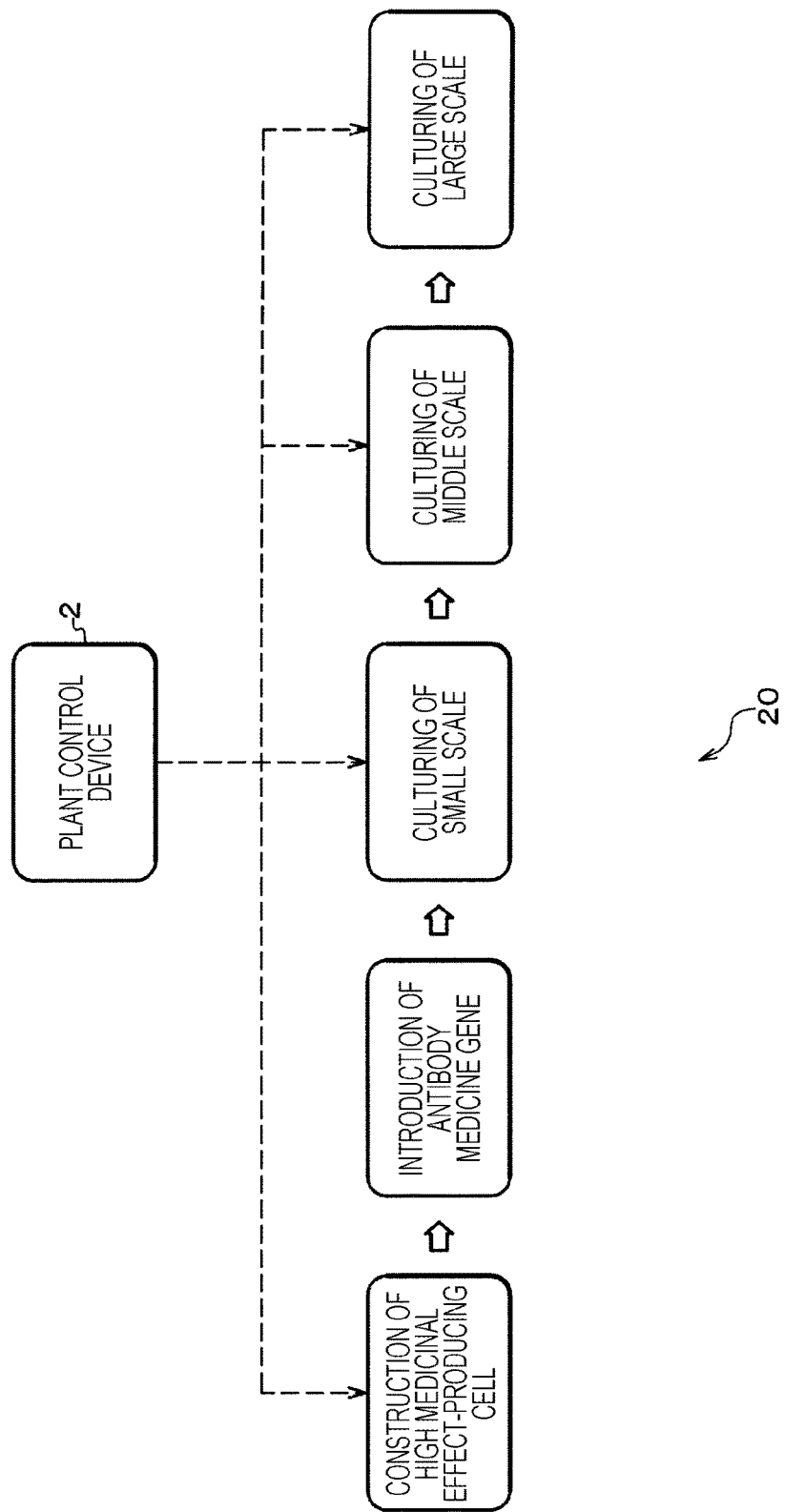
FIG. 9 is a schematic diagram of a medicine producing process in personalized medical care according to the embodiment.

FIG. 9 is a schematic diagram of the medicine producing process in personalized medical care according to the present embodiment.

In a pharmaceutical manufacturing plant 20, first, a high efficacy-producing cell is built, and an antibody medicine gene is introduced thereinto. Here, the high efficacy-producing cell is an animal cell into which a gene to promote the glycosylation required for production of the pharmaceutical according to the present embodiment is incorporated. Hereinafter, the high efficacy-producing cell is referred to as the cell strain in some cases.

The antibody medicine gene is a gene which produces pharmaceuticals to be the production target.

Here, a cell strain constructing unit 215 (FIG. 4) of a plant control device 2 conducts the building of cell strain through the adjustment of the time for introduction of chemicals such as nucleic acid degrading enzyme or reverse transcriptase, restriction enzyme, and DNA (Deoxyribonucleic Acid) ligase or the temperature, and the pH and the like. The information such as the time for introduction of chemicals or the temperature and pH for the building of cell strain is stored in a database 220 in advance.

The cell strain into which the antibody medicine gene is introduced is cultured through small-scale culture, medium-scale culture, and large-scale culture. The small-scale culture, the medium-scale culture, and the large-scale culture are distinguished from one another by the size of the culture vessel. For example, the small-scale culture is culture conducted by using a small instrument such as a dish or a flask, and the large-scale culture is culture conducted by using large equipment such as a tank. The medium-scale culture is culture conducted by using a smaller tank than in the large-scale culture.

As illustrated in FIG. 9, the plant control device 2 according to the present embodiment conducts the building of cell strain (high efficacy-producing cell) and the control of small-scale culture, medium-scale culture, and large-scale culture. Incidentally, the medicine production in personalized medical care is finished by the small-scale culture in a case and the large-scale culture in another case. In other words, production of the pharmaceutical for an individual is finished by the small-scale culture, and production of the pharmaceutical for a certain group is finished by the medium-scale culture or the large-scale culture. The certain group is a group having a common allergy or a group having a certain constitution.

Figure 10:
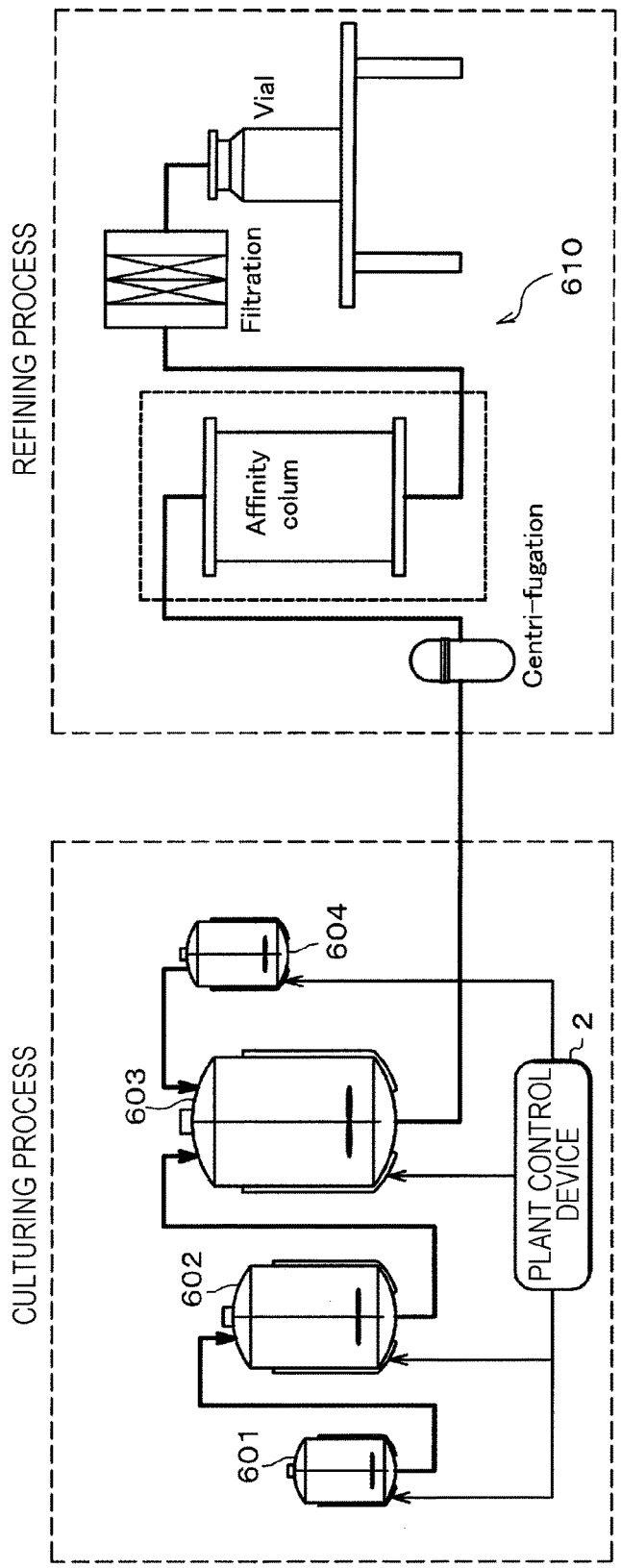
FIG. 10 is a diagram illustrating an example of a medicine producing plant according to the embodiment.

FIG. 10 is a diagram illustrating an example of a medicine producing plant according to this embodiment.

The process which is performed in the medicine producing plant installed in the pharmaceutical manufacturing plant 20 (FIG. 4) generally includes a culturing process using a bioreactor or the like or a purifying process using a purifying device 610 as illustrated in FIG. 10. Since a cell strain and the culturing process closely cooperate with each other in producing a medicine as a personalized medical care target, cell strains as expendables and culturing process devices suitable for the cell strains are provided in addition to the bioreactors 601 to 604 or the purifying device 610.

As illustrated in FIG. 10, the plant control device 2 controls the tanks 601 to 604 or the like in the culturing tank.

Figure 11:
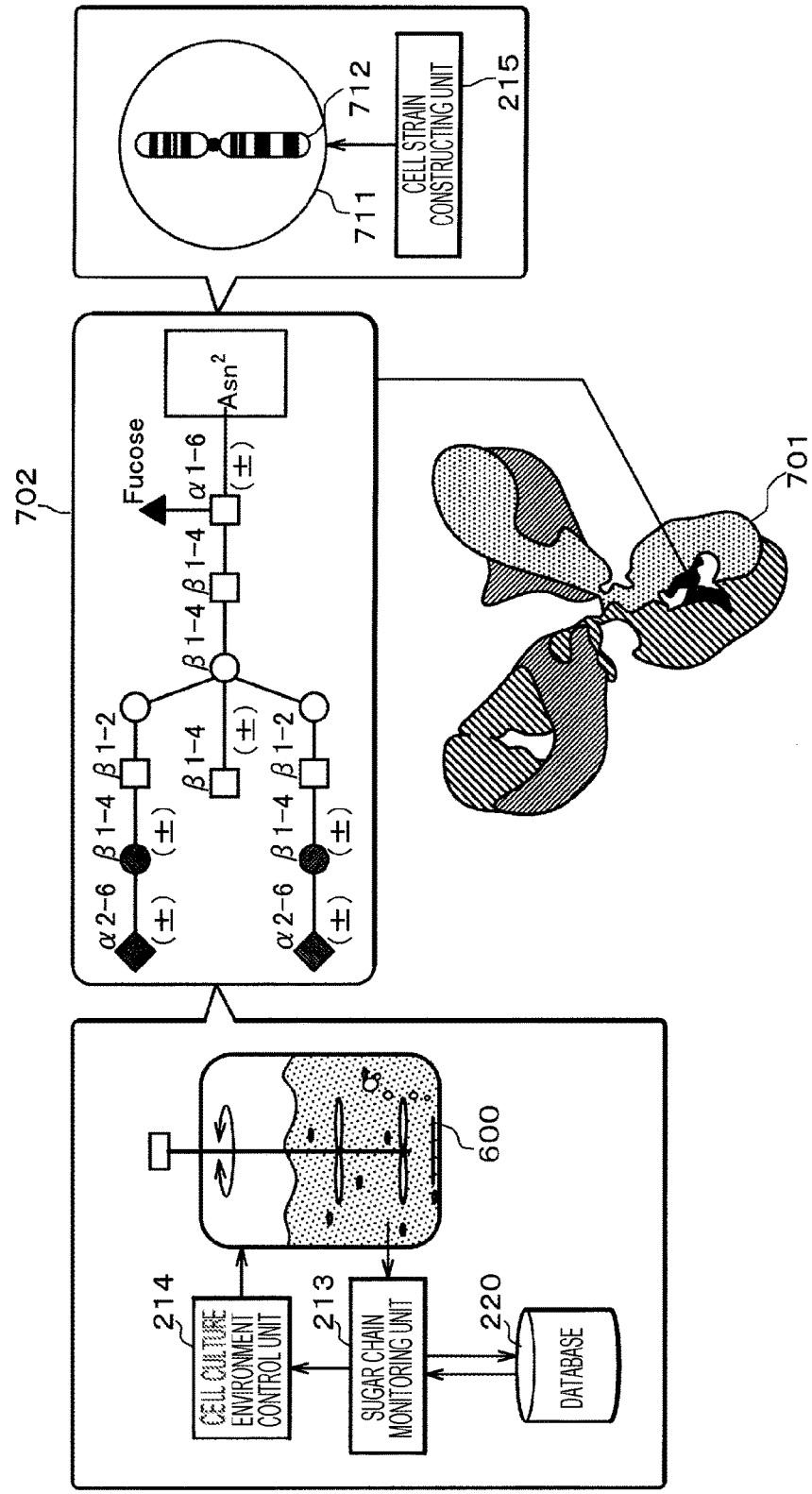
FIG. 11 is a diagram illustrating plant control according to the embodiment.

FIG. 11 is a diagram illustrating plant control according to this embodiment.

Antibody protein 701 included in the medicine used in this embodiment has a structure in which a sugar chain 702 is bonded to a part thereof.

The antibody protein 701 is generated by introducing an antibody medicine gene 712 as a control-responsible gene for generating the antibody protein 701 into the cell strain 711.

Identification of the antibody medicine gene 712 is performed by performing phenotype-genotype analysis on the phenotype of a patient.

By constructing a cell strain causing a high medicinal effect using glycosylation control, it is possible to control production of a medicine in which cells and a culturing process are integrated.

In producing a medicine using the antibody medicine gene 712, optimization of a glycosylation reaction in a cell strain due to gene recombination is important. First, identification of the antibody medicine gene 712 by phenotype-genotype analysis is performed by the cell strain constructing unit 215, and then the gene recombination using the antibody medicine gene 712 as a target is performed on the cell strain 711 constructed by the cell strain constructing unit 215 by the user, whereby the antibody medicine gene 712 is introduced.

The cell strain 711 into which the antibody medicine gene 721 is introduced is cultured in the bioreactor 600. At this time, the sugar chain monitoring unit 213 of the plant control device 2 monitors a sugar chain concentration in the bioreactor 600. The sugar chain monitoring unit 213 always compares the cell culture environment information in the database 220 with the sugar chain concentration and outputs the cell culture environment information based on the comparison result to the cell culture environment control unit 214. The cell culture environment control unit 214 controls the cell culture environment of the bioreactor 600 on the basis of the input cell culture environment information.

By performing this control, uniform glycosylation with a small deviation can be performed and a homogenous medicine can be produced.

In this embodiment, the sugar chain monitoring unit 213 monitors the sugar chain concentration so as to satisfy the cell culture environment included in the plant control information which has been transmitted from the central control device 1 and stored in the database 220. However, the present invention is not limited to this example, but data (correlation data) in which the sugar chain concentrations in the bioreactor 600 and the cell culture environments are correlated with each other may be stored in the database 220. The sugar chain monitoring unit 213 may monitor the cell culture environment in the bioreactor 600 on the basis of the current sugar chain concentration in the bioreactor 600 and the correlation data in the database 220. Accordingly, it is possible to suppress distribution of glycosylation patterns and to perform uniform glycosylation.

In order to perform uniform glycosylation, reaction steps of a glycosylation reaction path have to be efficiently and surely performed. The reaction steps include a reaction step affecting gene expression of a cell and a reaction step affecting the culturing process. As described above, in order to perform uniform glycosylation, it is necessary to perform construction of a cell strain by gene recombination and the culturing process corresponding to the cell strain.

<Glycosylation Control Type Medicine Producing Process>

Figure 12:
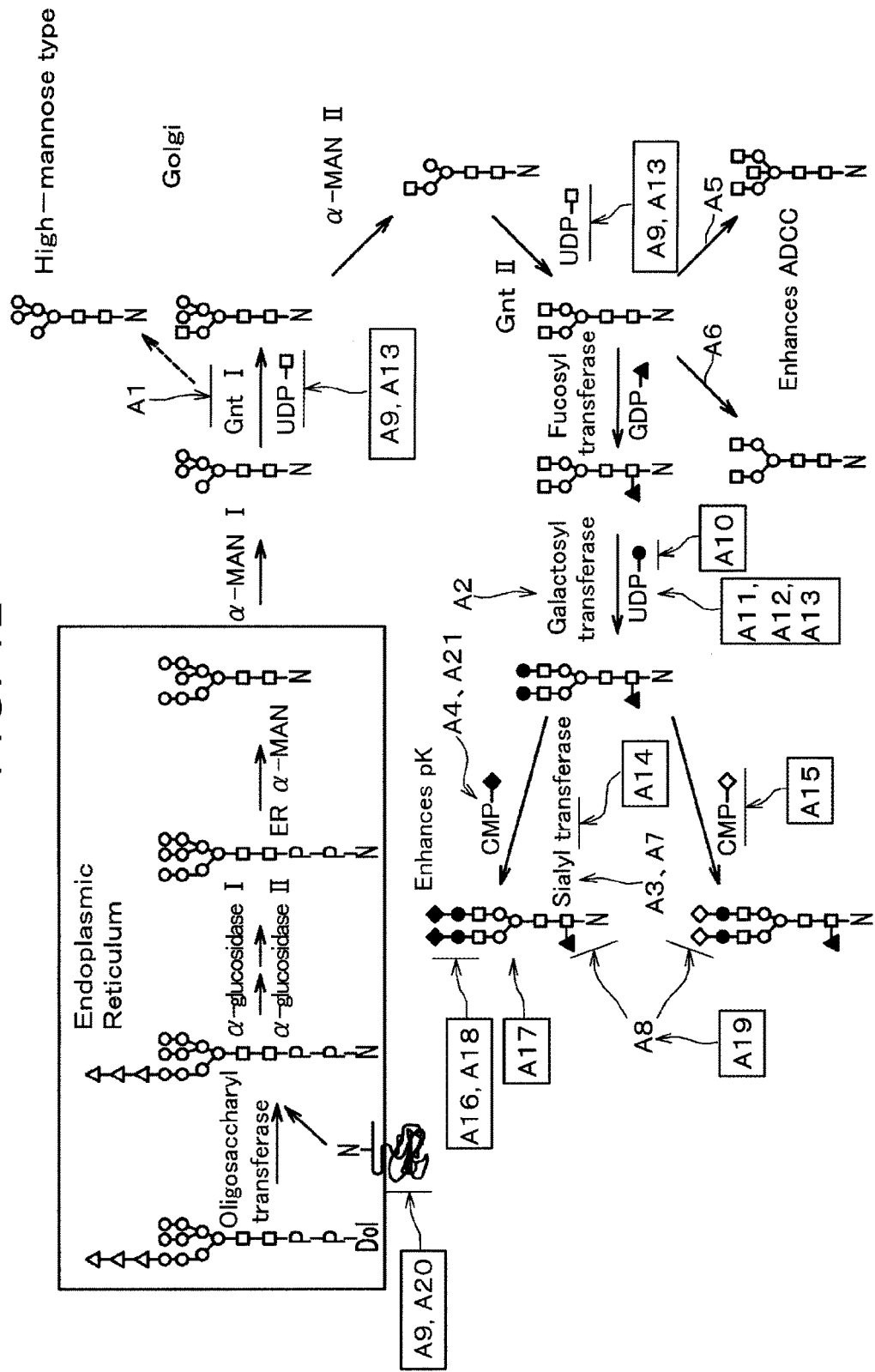
FIG. 12 is a diagram illustrating an example of a reaction path of glycosylation in an antibody medicine.

FIG. 12 is a diagram illustrating an example of a reaction path of glycosylation in an antibody medicine.

In FIG. 12, the A1 to A21 treatment means the following treatment. Here, the plant control device 2 conducts control of the treatment enclosed in a square among the A1 to A21 treatment illustrated in FIG. 12.

(Gene Control)

(A1) GntI−/−Lec1 Mutant

The GntI gene and Lec1 gene in a cell are knocked out. A high-mannose type sugar chain is added to the antibody protein by this. The antibody-dependent cellular cytotoxicity (ADCC) activity is inhibited, or the half-life is shortened.

(A2) β(1,4)-GalT+

The β(1,4)-GalT gene in a cell is knocked in. The terminal of N-acetylglucosamine (GlcNAc) is cut.

(A3) α(2,3)-Sialyltransferase+

The α(2,3)-Sialyltransferase (sialyltransferase) gene in a cell is knocked in. Sialylation to the sugar chain is conducted.

(A4) CMP-sialic acid transporter+

The CMP-sialic acid transporter gene in a cell is knocked in, and the sialic acid is increased.

(A5) Gnt III+ Mutant

The Gnt III gene in a cell is knocked in. N-acetylglucosamine (GlcNAc) is bisected, and the antibody-dependent cellular cytotoxicity (ADCC) activity is increased.

(A6) Fut8−/− Mutant

The Fut8 gene in a cell is knocked out, and fucosylation is conducted.

(A7) Antisense RNA sialidase

The antisense RNA sialidase in a cell is knocked in, and extracellular sialylation enzymatic activity is inhibited.

(A8) Sialidase activity

Sialylation is inhibited by an increase in extracellular sialidase.

(Medium and Culture Process)

(A9) Addition of low concentration glucose or low concentration glutamine (less than 1 mM).

(A10) Change in low dissolved oxygen concentration (less than 10%).

(A11) Change in pH concentration (pH 6.8 to 7.8).

(A12) Addition of manganese.

(A13) Addition of sodium butyrate.

(A14) Increase in ammonia concentration.

(A15) Change in high dissolved carbon dioxide (>100 mmHg).

(A16) Addition of dimethyl sulfoxide (DMSO).

(A17) Addition of glycerol.

(A18) Lowering of temperature (30 to 32° C.)

(A19) Lowering of survival rate.

(A20) Application of high shear stress.

(A21) Addition of N-acetylmannosamine.

The user conducts the culture of the built cell strain and examines the change of glycosylation depending on the culture environment in advance through a culture experiment. Examples of the culture environment to be changed may include the glucose concentration, the dissolved oxygen concentration, the dissolved carbon dioxide concentration, the pH, the manganese concentration, the sodium bicarbonate concentration, the ammonia concentration, the dimethyl sulfoxide (DMSO) concentration, the glycerol concentration, the temperature, the N-acetylmannosamine concentration, and the shear stress. These culture environments are included in plant control information 92. Meanwhile, DMSO is a chemical that is used to dissolve a certain reagent in the medium, and the shear stress is an external force to break up a cell or a protein. For example, the cell or protein is sheared off unless otherwise the culture solution is stirred by a force equal to or weaker than the shear stress.

In addition, the reactivity of glycosylation is different for every individual patient, and thus it is required to conduct glycosylation control suitable for the patient. It is possible to produce a desired medicine as the glucose concentration, the dissolved oxygen concentration, the dissolved carbon dioxide concentration, the pH, the manganese concentrations, the sodium bicarbonate concentration, the ammonia concentration, the DMSO concentration, the glycerol concentration, the temperature, the N-acetylmannosamine concentration, the shearing stress, and the like are controlled in the culture process.

<Conclusion>

As described above, in the technique described in PTL 1, since mixture of compounded medicines, that is, produced medicines, is controlled on the basis of the information, the variety of medicines to be produced are limited.

On the other hand, the medicine production support system Z according to this embodiment includes the plant control device 2 that controls a cell culture environment of a cell strain for producing a medicine in the pharmaceutical manufacturing plant 20 for producing the medicine and the central control device 1 that remotely controls the plant control device 2 on the basis of the information input from the outside. Accordingly, the medicine production support system Z according to this embodiment can produce various medicines.

In the medicine production support system Z according to this embodiment, since the central control device 1 controls the plant control device 2 on the basis of an inspection result of a patient, it is possible to produce a medicine capable of reducing a side effect depending on a patient's physical constitution without any human labor.

In the medicine production support system Z according to this embodiment, the central control device 1 converts the information such that private information of the patient is not referred to from the outside at the time of transmitting information to the outside. Accordingly, it is possible to protect the private information of a patient.

In the medicine production support system Z according to this embodiment, the cell strain includes a gene relevant to glycosylation. Accordingly, it is possible to produce a medicine based on glycosylation.

The medicine production support system Z according to this embodiment further includes the navigation device 3 that searches for a delivery route of a delivery vehicle for delivering a medicine on the basis of the traffic information 94. Accordingly, it is possible to rapidly deliver the medicine. Particularly, it is Possible to satisfactorily deliver a medicine at the time of disaster such as earthquake disaster.

In the medicine production support system Z according to this embodiment, the control device 1 transmits the control temperature information 93 which is information on the storage temperature of the medicine at the time of delivering the medicine and a temperature controller that controls the storage temperature of the medicine on the basis of the transmitted control temperature information 93 is further included. Accordingly, it is possible to store a medicine at an appropriate temperature without any human labor.

In the medicine production support system Z according to this embodiment, the central control device 1 determines allocation of a delivery vehicle for delivering the medicine on the basis of information on the inspection result. Accordingly, it is possible to determine allocation of an appropriate delivery vehicle without any human labor.

Second Embodiment

Figure 13:
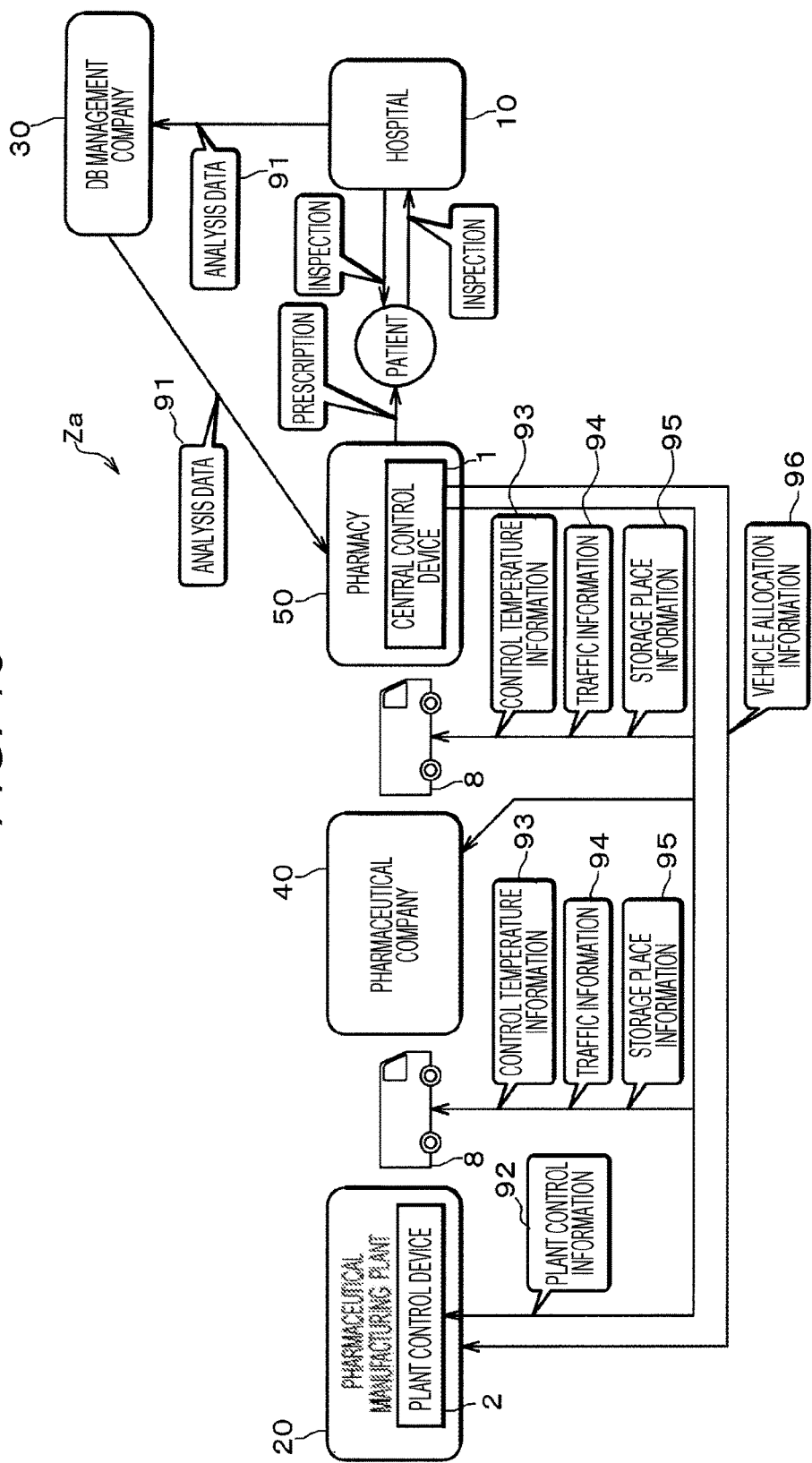
FIG. 13 is a diagram illustrating an example of a configuration of a medicine production support system according to a second embodiment.

FIG. 13 is a diagram illustrating an example of a configuration of a medicine production support system according to a second embodiment.

In FIG. 13, the same elements as illustrated in FIG. 1 will be referenced by the same reference signs and description thereof will not be repeated.

In the medicine production support system Za illustrated in FIG. 13, the central control device 1 is installed in a pharmacy 50. That is, the analysis data 91 is directly sent from the DB management company 30 to a pharmacist of the pharmacy 50. The analysis data 91 sent directly from the DB management company 30 preferably has a format for which private information is not referred to.

The other processes are the same as described in the first embodiment.

Accordingly, the pharmacist can check details of the analysis data 91 or the plant control information before the analysis data 91 is sent to the pharmaceutical manufacturing plant 20.

Third Embodiment

Figure 14:
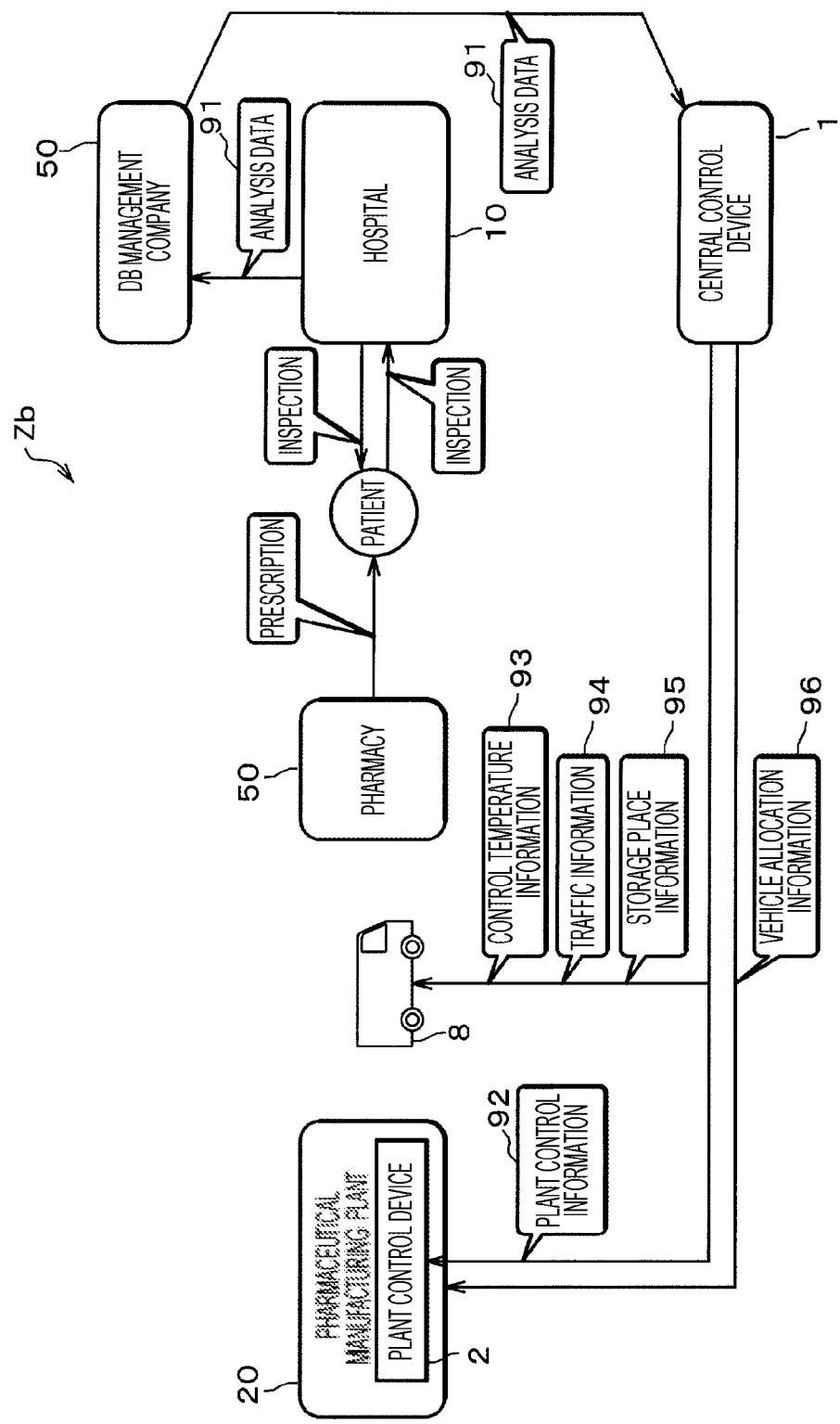
FIG. 14 is a diagram illustrating an example of a configuration of a medicine production support system according to a third embodiment.

FIG. 14 is a diagram illustrating an example of a configuration of a medicine production support system according to a third embodiment.

In FIG. 14, the same elements as illustrated in FIG. 1 will be referenced by the same reference signs and description thereof will not be repeated.

In the medicine production support system Zb illustrated in FIG. 14, the pharmaceutical company 40 in FIG. 1 is skipped and a produced medicine is delivered directly from the pharmaceutical manufacturing plant 20 to a pharmacy 50. That is, a wholesaler (the pharmaceutical company 40) does not intervene the middle way and a medicine is prescribed to a patient from the pharmaceutical manufacturing plant 20 via a pharmacist.

Accordingly, it is possible to save costs or times required for delivering a medicine and to efficiently deliver a medicine.

When a national system is changed and preparation by a pharmacist is not necessary, a medicine production support system in which a medicine is distributed directly from the pharmaceutical manufacturing plant 20 to a patient without passing through a pharmacist (a pharmacy 50) may be employed.

The medicine production support system Z according to this embodiment can be applied to improvement in target molecule selectivity of a companion diagnostic agent using an antibody. In the personalized medical care, a companion diagnostic agent for inspecting a medicine suitable for each patient or reactivity of the patient to the medicine before treatment is required to provide treatment suitable for each patient. A medicine used for the companion diagnostic agent has to have high selectivity to a target and an antibody is mainly used. In this case, according to the medicine production support system Z according to this embodiment, information on purification of each companion diagnostic agent is sent from the central control device 1 to the plant control device 2, and the plant control device 2 performs the plant control on the basis of the sent information.

In this embodiment, control of production of an antibody medicine is assumed, but the medicine production support system Z may control, for example, a reaction process (an order in which adenine (A), guanine (G), cytosine (C), and thymine (T) react) in a nucleic acid medicine. In this case, it is also possible to produce a medicine suitable for each patient. The medicine production support system Z according to this embodiment may be applied to production of a peptide medicine. That is, in organic synthetic chemistry, the medicine production support system Z controls a reaction process (a synthesis order of an amino acid or the like) and controls an amino acid sequence of peptide. Accordingly, it is possible to produce a medicine suitable for each patient.

In this embodiment, the central control device 1 deletes private information of a patient from the information to be transmitted to the outside such that the private information of the patient is not referred to from the outside, but the present invention is not limited to this configuration and may include an encryption processing unit that encrypts information when the central control device 1 transmits information to the outside. In this case, the plant control device 2, the navigation device 3, the temperature controller 4, and the vehicle allocation information display device 5 may include a decryption processing unit that decrypts the encrypted information.

When information is transmitted and received using a virtual private network (VPN), the information converting unit 117 of the central control device 1 may skipped and the processes of steps S103 and S112 in FIG. 8 may be skipped.

The present invention is not limited to the above-mentioned embodiments and includes various modified examples. For example, the above-mentioned embodiments are described in detail for the purpose of easy understanding of the present invention, but are not limited to have all the above-mentioned elements.

The configurations, the functions, the units 111 to 117, 211 to 215, 311 to 313, 411 to 413, and 511 to 513, the storage devices 120, 320, 420, and 520, the database 220, and the like which have been described above may be embodied by hardware by designing a part or all thereof, for example, in an integrated circuit or the like. As illustrated in FIGS. 3 to 7, the configurations, the functions, and the like which have been described above may be embodied by software by causing a processor such as the CPU 140, 240, 340, 440, or 540 to analyze and execute a program for embodying the functions. Information such as the program for embodying the functions, a table, and a file may be stored in a hard disk (HD) or may be stored on a recording device such as a memory or a solid state drive (SSD) or a recording medium such as an integrated circuit (IC) card, a secure digital (SD) card, or a digital versatile disc (DVD).

In the above-mentioned embodiments, only control lines or information lines which are considered to be necessary for explanation are mentioned, and all control lines or information lines in view of production are not mentioned. Actually, almost all the elements may be thought to be connected to each other.

REFERENCE SIGNS LIST 1 central control device (control device)
2 plant control device
3 navigation device (route search device)
4 temperature controller
5 vehicle allocation information display device
20 pharmaceutical manufacturing plant
91 analysis data
92 plant control information
93 control temperature information
94 traffic information
95 storage place information
113 information generating unit
114 vehicle allocation search unit
115 storage place search unit
117 information converting unit
213 sugar chain monitoring unit
214 cell culture environment control unit
215 cell strain constructing unit
313 route search unit
413 temperature control unit
513 display processing unit
701 antibody protein
702 sugar chain
711 cell strain
712 antibody medicine gene
Z, Za, Zb medicine production support system

The invention claimed is:

1. A medicine production support system comprising:
a plant control device that controls a cell culture environment of a cell strain for producing a medicine in a pharmaceutical manufacturing plant for producing the medicine; and
a control device that remotely controls the plant control device on the basis of information input from outside, the plant control device includes
a sugar chain monitoring unit,
a cell culture environment control unit, and
a cell strain construction unit,
wherein the cell strain construction unit identifies an antibody medicine gene and uses the antibody medicine gene as a target to construct the cell strain,
wherein the sugar chain monitoring unit monitors sugar chain concentration in the cell strain, compares the sugar chain concentration with cell culture environment information that is stored in a database, and outputs the comparison to the cell culture environment control unit, and
wherein the cell culture environment control unit controls the cell culture environment based on the comparison inputted by the sugar chain monitoring unit.

2. The medicine production support system according to claim 1, wherein the control device remotely controls the plant control device on the basis of information on an inspection result of a patient.

3. The medicine production support system according to claim 2, wherein the control device converts the information such that private information of the patient is not referred to from the outside at the time of transmitting information to the outside.

4. The medicine production support system according to claim 1, wherein the cell strain includes a gene relevant to glycosylation.

5. The medicine production support system according to claim 1, further comprising a route search device that searches for a delivery route of a delivery vehicle for delivering a medicine on the basis of traffic information which is information on a traffic condition,
wherein the control device transmits the traffic information to the route search device.

6. The medicine production support system according to claim 1, further comprising a temperature controller that controls a storage temperature of the medicine on the basis of control temperature information which is information on the storage temperature of the medicine,
wherein the control device transmits the control temperature information which is the information on the storage temperature of the medicine at the time of delivering the medicine to the temperature controller.

7. The medicine production support system according to claim 1, wherein the control device determines allocation of a delivery vehicle for delivering the medicine on the basis of information on an inspection result.

8. The medicine production support system according to claim 1, wherein the control device is installed in a pharmacy.

9. A medicine production support method, wherein
a control device transmits information input from outside to a plant control device in a pharmaceutical manufacturing plant, and
the plant control device produces a medicine by controlling a cell culture environment of a cell strain for producing the medicine on the basis of the transmitted information,
the plant control device includes
a sugar chain monitoring unit,
a cell culture environment control unit, and
a cell strain construction unit,
wherein the cell strain construction unit identifies an antibody medicine gene and uses the antibody medicine gene as a target to construct the cell strain, wherein the sugar chain monitoring unit monitors sugar chain concentration in the cell strain, compares the sugar chain concentration with cell culture environment information that is stored in a database, and outputs the comparison to the cell culture environment control unit, and wherein the cell culture environment control unit controls the cell culture environment based on the comparison inputted by the sugar chain monitoring unit.

10. The medicine production support method according to claim 9, wherein the control device controls the plant control device on the basis of information on an inspection result of a patient.

11. The medicine production support method according to claim 9, wherein the control device transmits traffic information to a route search device, and the route search device searches for a delivery route of a delivery vehicle for delivering a medicine on the basis of the transmitted traffic information.

12. The medicine production support method according to claim 9, wherein the control device transmits control temperature information which is information on a storage temperature of the medicine at the time of delivering the medicine to a temperature controller, and the temperature controller controls the storage temperature of the medicine on the basis of the control temperature information.

13. The medicine production support system according to claim 1, wherein the cell culture environment control unit controls the cell culture environment of a bioreactor for culturing the cell strain on the basis of plant control information which is information for controlling the plant control device.

14. The medicine production support system according to claim 13, wherein the plant control information includes information on a glucose concentration, a glutamine concentration, a dissolved oxygen concentration, pH, a manganese concentration, a sodium butyrate concentration, an ammonia concentration, a dissolved carbon hydroxide concentration, a dimethyl sulfoxide concentration, a glycerol concentration, a temperature, a cell survival rate, a shearing stress, and an N-acetylmannosamine concentration.

15. The medicine production support system according to claim 14, wherein the sugar chain monitoring unit monitors the sugar chain concentration in a bioreactor in which the cell strain is cultured and outputs the cell culture environment information which is information on an environment of the bioreactor to the cell culture environment control unit on the basis of the sugar chain concentration.

16. The medicine production support system according to claim 15, wherein the cell strain constructing unit constructs the cell strain which is cultured in the bioreactor.

17. The medicine production support method according to claim 9, wherein the information transmitted from the control device includes information on a glucose concentration, a glutamine concentration, a dissolved oxygen concentration, pH, a manganese concentration, a sodium butyrate concentration, an ammonia concentration, a dissolved carbon hydroxide concentration, a dimethyl sulfoxide concentration, a glycerol concentration, a temperature, a cell survival rate, a shearing stress, and an N-acetylmannosamine concentration.

18. The medicine production support method according to claim 17, wherein the plant control device monitors the sugar chain concentration in a bioreactor in which the cell strain is cultured and outputs cell culture environment information which is information on an environment of the bioreactor on the basis of the sugar chain concentration to control the environment of the bioreactor.

19. The medicine production support method according to claim 18, wherein the plant control device constructs the cell strain which is cultured in the bioreactor.

* * * * *